US012751970B2

(12) United States Patent
Ju et al.

(10) Patent No.: US 12,751,970 B2
(45) Date of Patent: Oct. 6, 2026

(54) USE OF POROUS CALCIUM-BASED GRANULES FOR PROMOTING HEALING OF AN INTRA-ARTICULAR OR PERI-ARTICULAR FRACTURE OF A FRACTURED BONE

(71) Applicant: JOY MEDICAL DEVICES CORPORATION, Kaohsiung (TW)

(72) Inventors: Chien-Ping Ju, Kansas City, MO (US); Jiin-Huey Chern Lin, Winnetka, IL (US); Tai-Hua Yang, Tainan (TW); Yi-Chuan Chou, Tainan (TW)

(73) Assignee: JOY MEDICAL DEVICES CORPORATION, Kaohsiung (TW)

( * ) Notice: Subject to any disclaimer, the term of this patent is extended or adjusted under 35 U.S.C. 154(b) by 522 days.

(21) Appl. No.: 18/511,313

(22) Filed: Nov. 16, 2023

(65) Prior Publication Data

US 2025/0161352 A1 May 22, 2025

(51) Int. Cl.

| | |
|---|---|
| ***A61K 33/42*** | (2006.01) |
| ***A61K 9/16*** | (2006.01) |
| ***A61K 33/06*** | (2006.01) |
| ***A61L 27/56*** | (2006.01) |
| ***A61L 27/58*** | (2006.01) |
| ***A61P 19/02*** | (2006.01) |

(52) U.S. Cl.

CPC ................ *A61K 33/42* (2013.01); *A61K 9/16* (2013.01); *A61K 33/06* (2013.01); *A61L 27/56* (2013.01); *A61L 27/58* (2013.01); *A61P 19/02* (2018.01)

(58) Field of Classification Search

None

See application file for complete search history.

(56) References Cited

U.S. PATENT DOCUMENTS 8,784,551 B2 * 7/2014 Ju ......................... C04B 41/009
106/35

OTHER PUBLICATIONS

Tyllianakis et al. "Use of Injectable Calcium Phosphate in the Treatment of Intra-Articular Distal Radius Fractures" 2003.*

Yang et al; Research Article for Osteoregenerative efficacy of a novel synthetic, resorbable Ca/P/S-based bone graft substitute in intra- and peri-articular fractures: a brief medical image-based report; Journal of Orthopaedic Surgery and Research (2022).

* cited by examiner

*Primary Examiner* — Danah Al-Awadi

(74) *Attorney, Agent, or Firm* — BACON&THOMAS,PLLC

(57) ABSTRACT

A method for promoting healing of an intra-articular or peri-articular fracture of a fractured bone in a patient is provided, which involves administering porous calcium-based granules into a joint having a fractured bone with an intra-articular or peri-articular fracture and/or administering the porous calcium-based granules to the intra-articular or peri-articular fracture of the fractured bone during or after the fractured bone being fixed through a surgery in the patient.

14 Claims, 4 Drawing Sheets

Fig. 4
Post –OP
1 day
Post –OP
2 months

USE OF POROUS CALCIUM-BASED GRANULES FOR PROMOTING HEALING OF AN INTRA-ARTICULAR OR PERI-ARTICULAR FRACTURE OF A FRACTURED BONE

FIELD OF THE INVENTION

The present invention is related to a novel use of porous calcium-based granules for promoting healing of an intra-articular or peri-articular fracture of a fractured bone.

BACKGROUND OF THE INVENTION

When a fracture goes into or around a joint, it usually damages the cartilage at the ends of bones and other joint tissue. As a result, the affected joints are prone to traumatic arthritis, leading to stiffness. Repairing bone damage, maintaining joint integrity, and avoiding subchondral and metaphyseal defects caused by comminuted fractures is often a great challenge for orthopedic surgeons. Tissue engineering of synthetic bone substitutes has proven beneficial to the attachment and proliferation of bone cells, promoting the formation of mature tissues with sufficient mechanical strength and has become a promising alternative to autograft methods. An ideal bone graft substitute should present such material properties as biocompatibility, resorbability, vascularity and angiogenesis, durability, osteogenesis and osteoconduction/osteoinduction. However, in vitro and in vivo studies indicated that most of the artificial bone products in the current market, such as calcium phosphate and recombinant human bone morphogenetic protein, are poorly absorbed and uncertain in biocompatibility, even induce ectopic cartilage and bone formation or abnormal synostosis [1-6].

There is a need to promote healing of an intra-articular or peri-articular fracture of a fractured bone for early rehabilitation by preventing soft tissue adhesions and joint contractures, moreover, avoiding ectopic bone formation or abnormal synostosis.

SUMMARY OF THE INVENTION

An objective of this invention is to provide a use of porous calcium-based granules in the fabrication of a medicament for promoting healing of an intra-articular or peri-articular fracture of a fractured bone after being fixed through a surgery in a patient, wherein the porous calcium-based granules have a porosity of about 30 vol % to about 90 vol % and a granular size of about 0.1 mm to about 2.5 mm, and the porous calcium-based granules comprise calcium phosphate, calcium sulfate, calcium carbonate, calcium oxide, calcium hydroxide, hydroxyapatite, or a combination thereof.

Another objective of this invention is to provide a method for promoting healing of an intra-articular or peri-articular fracture of a fractured bone in a patient, comprising administering porous calcium-based granules into a joint having a fractured bone with an intra-articular or peri-articular fracture and/or administering the porous calcium-based granules to the intra-articular or peri-articular fracture of the fractured bone during or after the fractured bone being fixed through a surgery in the patient, wherein the porous calcium-based granules have a porosity of about 30 vol % to about 90 vol % and a granular size of about 0.1 mm to about 2.5 mm, and the porous calcium-based granules comprise calcium phosphate, calcium sulfate, calcium carbonate, calcium oxide, calcium hydroxide, hydroxyapatite, or a combination thereof.

Preferably, the promoting of healing of an intra-articular or peri-articular fracture of a fractured bone is free of soft tissue adhesions, joint contractures, ectopic bone formation, abnormal synostosis, or a combination thereof near the fracture bone in the patient.

Preferably, the porosity of the porous calcium-based granules is of about 60 vol % to about 80 vol %.

Preferably, the granular size the porous calcium-based granules is of about 0.5 mm to about 1.5 mm.

Preferably, pores of the porous calcium-based granules have a pore size in a range of about 30 μm to about 300 μm.

Preferably, pores of the porous calcium-based granules comprise interconnected pores.

Preferably, the porous calcium-based granules comprise calcium phosphate, calcium sulfate, hydroxyapatite or a mixture thereof.

Preferably, the porous calcium-based granules comprise a mixture of hydroxyapatite, calcium phosphate and calcium sulfate.

Preferably, the calcium phosphate is tetracalcium phosphate (TTCP), dicalcium phosphate, tricalcium phosphate, monocalcium phosphate or a mixture thereof; and the calcium sulfate is calcium sulfate hemihydrate (CSH), calcium sulfate dihydrate (CSD), anhydrous calcium sulfate, or a mixture thereof.

Preferably, the calcium phosphate is tetracalcium phosphate (TTCP), dicalcium phosphate, or a mixture thereof; and the calcium sulfate is calcium sulfate hemihydrate (CSH), calcium sulfate dihydrate (CSD), or a mixture thereof.

DETAILED DESCRIPTION OF THE INVENTION

Materials and Methods

A synthetic, inorganic and highly porous Ca/P/S-based bone-substituting material (Ezechbone® Granule, CBS- 400) was used by the doctors. CBS-400 is mainly comprised of hydroxyapatite (HA) and calcium sulfate dihydrate (CSD) with a delicate Ca/P/S atomic ratio of 54.6/39.2/6.2.

EZECHBONE® Granule is available from JOY MEDICAL DEVICES CORPORATION, 1F., No. 63, Luke 2nd Road, Luzhu District, Kaohsiung City, Taiwan. EZECHBONE® Granule has a particle size of about 0.4-1.2 mm, and a porosity of about 70-80 vol %, and is TTCP/DCPA/CSH-derived porous granules prepared based on the method disclosed in U.S. Pat. No. 8,784,551. The porous granules of calcium compound can be prepared from a mixed powers of TTCP/DCP/calcium sulfate (preferably TTCP/DCPA/CSH; more preferably TTCP/DCPA/CSH/CSD) and a pore forming agent, which is then mixed with a $NH^{4+}$ solution to form a paste. The paste is hardened into a block in a mold, followed by washing the pore forming agent from the hardened block and breaking the block into porous granules; or breaking the block prior to washing. The porous granules are composed of hydroxyapatite, calcium sulfate (primarily CSD), and less significantly unreacted TTCP, DCP, and CSH. (DCPA: dicalcium phosphate anhydrous).

Figure 1:
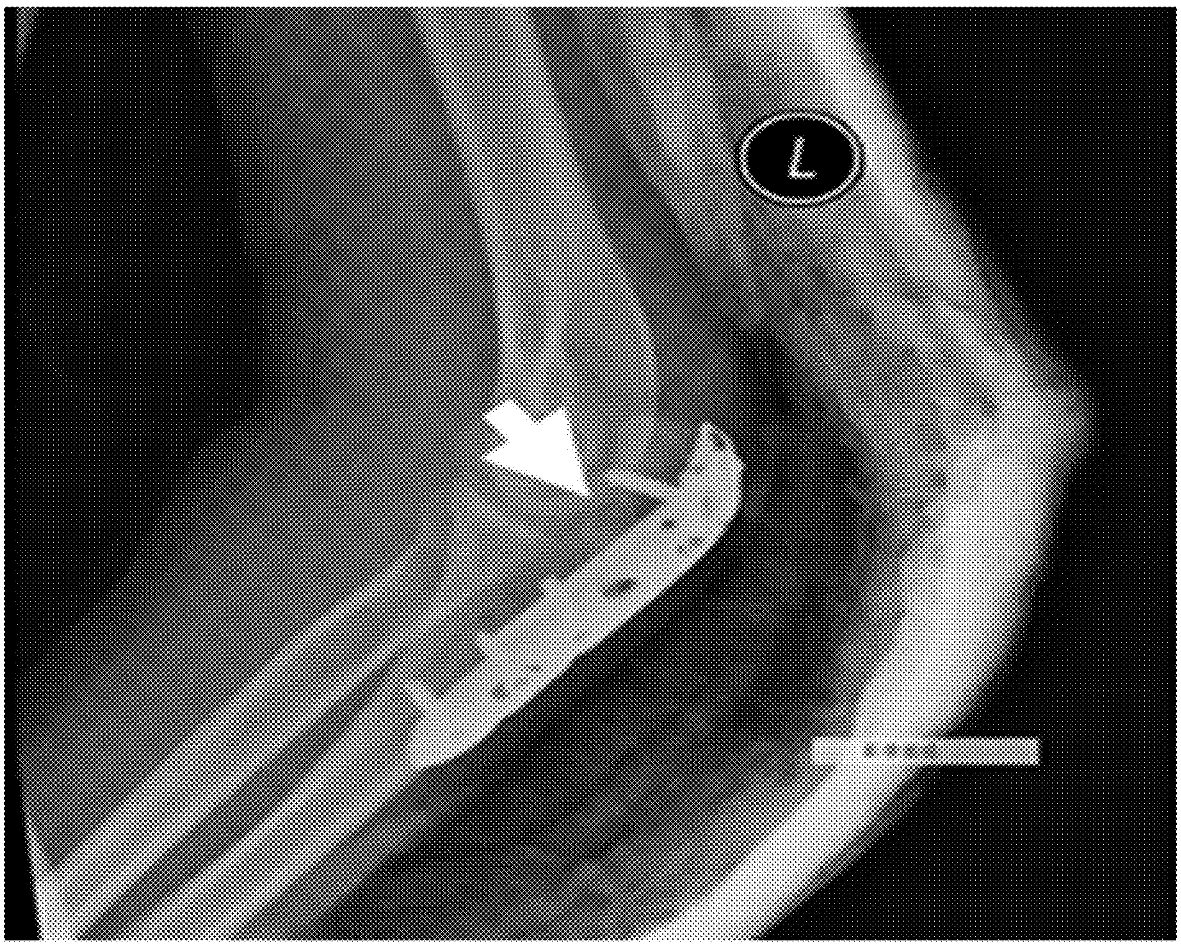
FIG. 1 is an image of a surgical site located in olecranons taken by X-rays two weeks after the surgery, wherein the nidus-like appearance (white arrow) in the X-ray image indicates a primary fusion of the bone substitute and its close contact with the surrounding bone.
Figure 2:
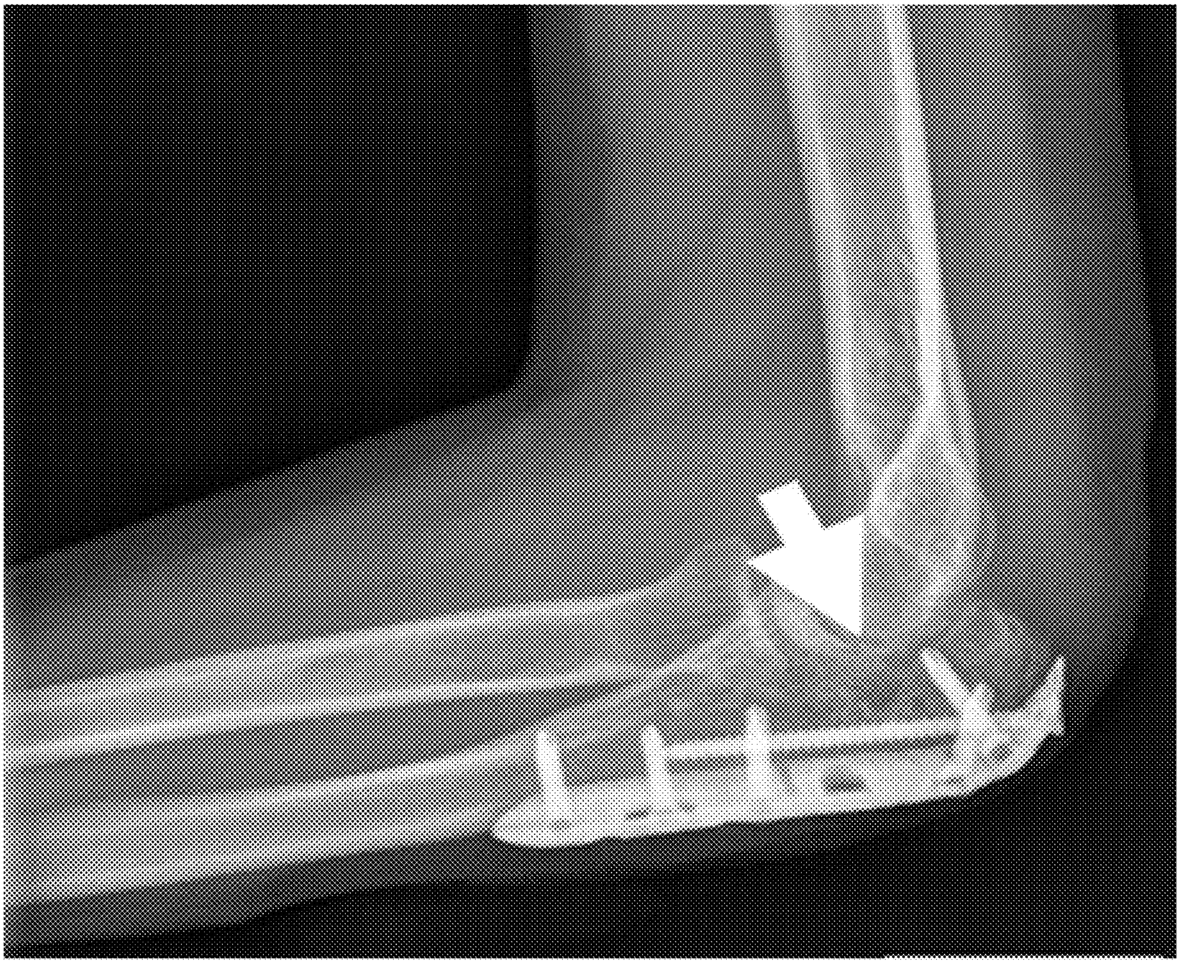
FIG. 2 is an X-rays image of the surgical site shown in FIG. 1 which was taken six weeks after the surgery, wherein the X-ray image reveals a shrinkage of the nidus-like lesion (white arrow) accompanied with initial bone callus formation.
Figure 3:
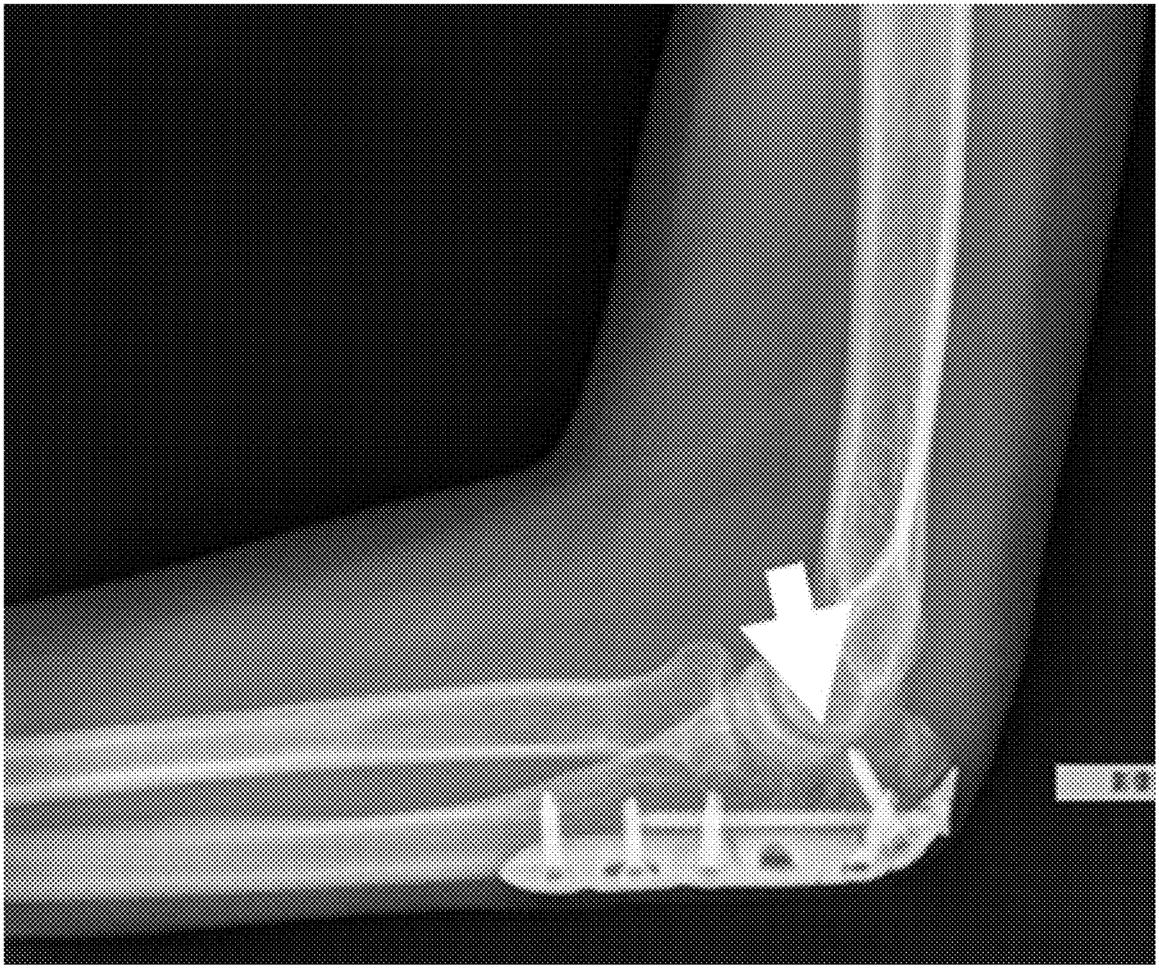
FIG. 3 is an X-rays image of the surgical site shown in FIG. 1 which was taken 12 weeks after the surgery, wherein the X-ray image reveals fill-full of the nidus-like lesion (white arrow) in bone graft area, demonstrating well healing of the bone.

According to the operation notes from the medical records, we collected fourteen cases of complex intra- and peri-articular fractures with Ezechbone® Granule bone grafting between 2019/11 and 2021/11. We studied the evidence of bone healing by reviewing, interpreting and analyzing the medical image recordings. All imaging images were reviewed, discussed and interpreted by an orthopedic surgeon with 15+ years of clinical experience in the field along with a diagnostic radiologist with 20+ years of experience. As indicated in X-ray, the initial bone graft area had turned into a nidus-like appearance (FIG. 1) several days following grafting, indicating a primary fusion The shrinkage of the nidus-like lesion (FIG. 2) suggested the initial bone callus formation. The fill-full of the nidus-like lesion (FIG. 3) indicated that the bone healed well. The time required for each different stage was recorded.

Results

Figure 4:
FIG. 4 are images of a surgical site located in metacarpal bones taken by X-rays one day (left) and two months (right) after the surgery, wherein the X-ray image shows that the bone substitute material was scattered in the soft tissue around the bone graft area and around the adjacent joint (white arrow) due to the treatment process (left); and these implant residues were entirely absorbed (white arrow) within two months after implantation (right).

From November 2019 to November 2021, we followed 14 cases (Table 1), including 11 males and 3 females, with an average of 34.1±9.8 y/o. The fracture types applying bone graft substitutes included 6 peri-articular and 8 intra-articular fractures. The surgical sites were located in two olecranons, two in the distal radius, two at the base of the proximal phalanx, four in the scaphoid, one in the radial head, and three in the metacarpal bones individually. According to medical image interpretation of X-rays, the time to nidus-like formation after bone grafting was 2.3±0.5 weeks; the time to initial callus formation was 4.7±1.0 weeks; and the time to good healing was 10.3±1.3 weeks. In four of the 14 cases, the bone substitute material was scattered in the soft tissue around the bone graft area and around the adjacent joint due to the treatment process (FIG. 4). These implant residues were entirely absorbed within 1.6±0.5 months, for these four cases, and there was no ectopic exostoses formation or synostosis with limited joint mobility. The initial ROM rehabilitation program started on average at 3.0±0.9 weeks. In addition, active joint range of motion and function was restored in all 14 followed-up cases on average at 3.5 months.

TABLE 1

Demographic Data and Clinical Image Characteristics

| case number | gender | age (y/o) | fracture type | fracture site | nidus-like formation (weeks) | initial callus formation (weeks) | healing well (weeks) | initial start to rehabilitation program (weeks) |
|---|---|---|---|---|---|---|---|---|
| 1 | F | 34 | intra-articular | olecraon | 2 | 6 | 12 | 3 |
| 2 | M | 26 | intra-articular | scaphoid | 2 | 6 | 12 | 4 |
| 3 | M | 34 | peri-articular | metacarpal neck | 3 | 5 | 10 | 2 |
| 4 | M | 31 | intra-articular | scaphoid | 2 | 4 | 8 | 4 |
| 5 | M | 38 | peri-articular | metacarpal base | 3 | 6 | 10 | 2 |
| 6 | M | 23 | intra-articular | radial head | 2 | 4 | 10 | 6 |
| 7 | F | 55 | intra-articular | metacarpal base | 3 | 5 | 10 | 2 |
| 8 | F | 20 | peri-articular | proximal phalanx | 2 | 4 | 10 | 2 |
| 9 | M | 44 | peri-articular | proximal phalanx | 2 | 4 | 8 | 2 |
| 10 | M | 31 | intra-articular | scaphoid | 2 | 4 | 12 | 4 |
| 11 | M | 23 | peri-articular | distal radius | 3 | 5 | 10 | 3 |
| 12 | M | 44 | intra-articular | scaphoid | 2 | 3 | 10 | 2 |
| 13 | M | 46 | peri-articular | distal radius | 2 | 4 | 10 | 4 |
| 14 | M | 28 | intra-articular | olecranon | 2 | 6 | 12 | 4 |

Discussion

It is generally recognized that, in clinical orthopedics, the treatment of complicated fracture, bone defects, delay- or non-union is a challenging and difficult issue. The bone substitute used in the present study (Ezechbone® Granule CBS-400) was observed to quickly integrate into surrounding bone within three weeks after grafting, while the initial callus formation of calcified deposits could be found within six weeks, indicating the early stage of repair. To the end of the follow-up, all of these cases healed entirely within three months. In addition, the CBS-400-derived earlier callus formation in the early stage of repair made it possible for us to shorten the start time of rehabilitation from 4-6 weeks after surgery to within 3 weeks. As a result, the patient may return to daily life function after 3.5 months of follow-up and rehabilitation treatment.

REFERENCES

1. Hirota S, Takaoka K, Hashimoto J, Nakase T, Takemura T, Morii E, et al. Expression of mRNA of murine bone-related proteins in ectopic bone induced by murine bone morphogenetic protein-4. Cell Tissue Res. 1994; 277:27-32.
2. Kim C S, Kim J I, Kim J, Choi S H, Chai J K, Kim C K, et al. Ectopic bone formation associated with recombinant human bone morphogenetic proteins-2 using absorbable collagen sponge and beta tricalcium phosphate as carriers. Biomaterials. 2005; 26:2501-7.
3. Habibovic P, de Groot K. Osteoinductive biomaterials—properties and relevance in bone repair. J Tissue Eng Regen Med. 2007; 1:25-32.
4. Habibovic P, Kruyt M C, Juhl M V, Clyens S, Martinetti R, Dolcini L, et al. Comparative in vivo study of six hydroxyapatite-based bone graft substitutes. J Orthop Res. 2008; 26:1363-70.
5. Song G, Habibovic P, Bao C, Hu J, van Blitterswijk C A, Yuan H, et al. The homing of bone marrow MSCs to non-osseous sites for ectopic bone formation induced by osteoinductive calcium phosphate. Biomaterials. 2013; 34:2167-76.
6. Wang L, Zhang B, Bao C, Habibovic P, Hu J, Zhang X. Ectopic osteoid and bone formation by three calcium-phosphate ceramics in rats, rabbits and dogs. PLOS One. 2014; 9: e107044.

The invention claimed is:

1. A method for promoting healing of an intra-articular or peri-articular fracture of a fractured bone in a patient, comprising administering porous calcium-based granules into a joint having a fractured bone with an intra-articular or peri-articular fracture and/or administering the porous calcium-based granules to the intra-articular or peri-articular fracture of the fractured bone during or after the fractured bone being fixed through a surgery in the patient, wherein the porous calcium-based granules have a porosity of about 30 vol % to about 90 vol % and a granular size of about 0.1 mm to about 2.5 mm, and the porous calcium-based granules comprise calcium phosphate, calcium sulfate, calcium carbonate, calcium oxide, calcium hydroxide, hydroxyapatite, or a combination thereof.

2. The method of claim 1, wherein the promoting of healing of an intra-articular or peri-articular fracture of a fractured bone is free of at least one of the following conditions: soft tissue adhesions, joint contractures, ectopic bone formation and abnormal synostosis near the fracture bone in the patient.

3. The method of claim 2, wherein the condition is soft tissue adhesions.

4. The method of claim 2, wherein the condition is joint contractures.

5. The method of claim 2, wherein the condition is ectopic bone formation.

6. The method of claim 2, wherein the condition is abnormal synostosis.

7. The method of claim 1, wherein the porosity is of about 60 vol % to about 80 vol %.

8. The method of claim 1, wherein the granular size is of about 0.5 mm to about 1.5 mm.

9. The method of claim 1, wherein pores of the porous calcium-based granules have a pore size in a range of about 30 μm to about 300 μm.

10. The method of claim 1, wherein pores of the porous calcium-based granules comprise interconnected pores.

11. The method of claim 1, wherein the porous calcium-based granules comprise calcium phosphate, calcium sulfate, hydroxyapatite or a mixture thereof.

12. The method of claim 1, wherein the porous calcium-based granules comprise a mixture of hydroxyapatite, calcium phosphate and calcium sulfate.

13. The method of claim 12, wherein the calcium phosphate is tetracalcium phosphate (TTCP), dicalcium phosphate, tricalcium phosphate, monocalcium phosphate or a mixture thereof; and the calcium sulfate is calcium sulfate hemihydrate (CSH), calcium sulfate dihydrate (CSD), anhydrous calcium sulfate, or a mixture thereof.

14. The method of claim 12, wherein the calcium phosphate is tetracalcium phosphate (TTCP), dicalcium phosphate, or a mixture thereof; and the calcium sulfate is calcium sulfate hemihydrate (CSH), calcium sulfate dihydrate (CSD), or a mixture thereof.

* * * * *